United States Patent [19]

Tay et al.

[11] Patent Number: 5,425,718
[45] Date of Patent: Jun. 20, 1995

[54] SELF-STICKING NEEDLE ASSEMBLY AND METHOD FOR INSERTION INTO AN ARTERY

[76] Inventors: Sew-Wah Tay, 18555 37th Ave. N., Plymouth, Minn. 55446; Thomas J. Holman, 5621 Thomas Ave. South, Minneapolis, Minn. 55410

[21] Appl. No.: 141,149

[22] Filed: Oct. 22, 1993

[51] Int. Cl.$^6$ .......................................... A61M 5/158
[52] U.S. Cl. ..................................... 604/165; 604/158
[58] Field of Search ................ 604/164, 165, 158, 274

[56] References Cited

U.S. PATENT DOCUMENTS

| | | | |
|---|---|---|---|
| 1,527,291 | 2/1925 | Zorraquin | 604/158 |
| 1,596,004 | 8/1926 | Bengoa . | |
| 2,623,521 | 12/1952 | Shaw . | |
| 3,506,007 | 4/1970 | Henkin . | |
| 3,515,137 | 6/1970 | Santomieri | 604/165 |
| 3,645,268 | 2/1972 | Capote . | |
| 3,727,613 | 4/1973 | Sorenson et al. | 604/165 |
| 4,292,970 | 10/1981 | Hession, Jr. . | |
| 4,362,156 | 12/1982 | Feller, Jr. | 604/165 |
| 4,428,379 | 1/1984 | Robbins et al. . | |
| 4,431,006 | 2/1984 | Trimmer et al. . | |
| 4,445,893 | 5/1984 | Bodicky | 604/165 |
| 4,497,325 | 2/1985 | Wedel . | |
| 4,512,351 | 4/1985 | Pohndorf . | |
| 4,645,491 | 2/1987 | Evans . | |
| 4,662,870 | 5/1987 | Augustine et al. . | |
| 4,667,679 | 5/1987 | Sahota . | |
| 4,760,847 | 8/1988 | Vaillancourt . | |
| 4,763,667 | 8/1988 | Manzo . | |
| 4,801,293 | 1/1989 | Jackson . | |
| 4,869,717 | 9/1989 | Adair . | |
| 4,881,551 | 11/1989 | Taylor . | |
| 4,887,606 | 12/1989 | Yock et al. . | |
| 4,898,178 | 2/1990 | Wedel . | |
| 4,907,599 | 3/1990 | Taylor . | |
| 4,911,691 | 3/1990 | Aniuk et al. . | |
| 4,919,653 | 4/1990 | Martinez et al. . | |
| 4,924,878 | 5/1990 | Nottke . | |
| 4,953,558 | 9/1990 | Akerfeldt . | |
| 4,966,589 | 10/1990 | Kaufman . | |
| 4,971,068 | 11/1990 | Sahi . | |
| 4,988,339 | 1/1991 | Vadher . | |
| 5,024,665 | 6/1991 | Kaufman . | |
| 5,036,860 | 8/1991 | Leigh et al. . | |
| 5,080,103 | 1/1992 | Olivier . | |
| 5,080,104 | 1/1992 | Marks et al. . | |
| 5,092,842 | 3/1992 | Bechtold et al. . | |
| 5,104,381 | 4/1992 | Gresl et al. . | |
| 5,127,909 | 7/1992 | Shichman | 604/165 |
| 5,131,394 | 7/1992 | Gelbach . | |
| 5,131,395 | 7/1992 | Gehlbach . | |
| 5,141,496 | 8/1992 | Dalto et al. . | |
| 5,158,552 | 10/1992 | Burgia et al. | 604/165 |
| 5,167,629 | 12/1992 | Vertenstein et al. . | |
| 5,186,712 | 2/1993 | Kelso et al. | 604/165 |
| 5,215,526 | 6/1993 | Deniega et al. . | |
| 5,215,528 | 6/1993 | Purdy et al. . | |
| 5,221,628 | 5/1993 | Marshall . | |
| 5,242,427 | 9/1993 | Bilweis | 604/164 |
| 5,261,891 | 11/1993 | Brinkerfoff et al. . | |

*Primary Examiner*—Paul J. Hirch
*Attorney, Agent, or Firm*—Willian Brinks Hofer Gilson & Lione

[57] ABSTRACT

The needle assembly of the present invention includes a rigid cannula with a blunt distal end, a needle housed inside the cannula, a hub on the needle for controlling the position of the distal end of the needle with respect to the distal end of the cannula and a stop connected to the cannula for limiting the distance of travel of the distal end of the needle. The preferred embodiment may also include a spring attached to the needle hub. The present invention also encompasses methods of using the needle assembly.

26 Claims, 2 Drawing Sheets

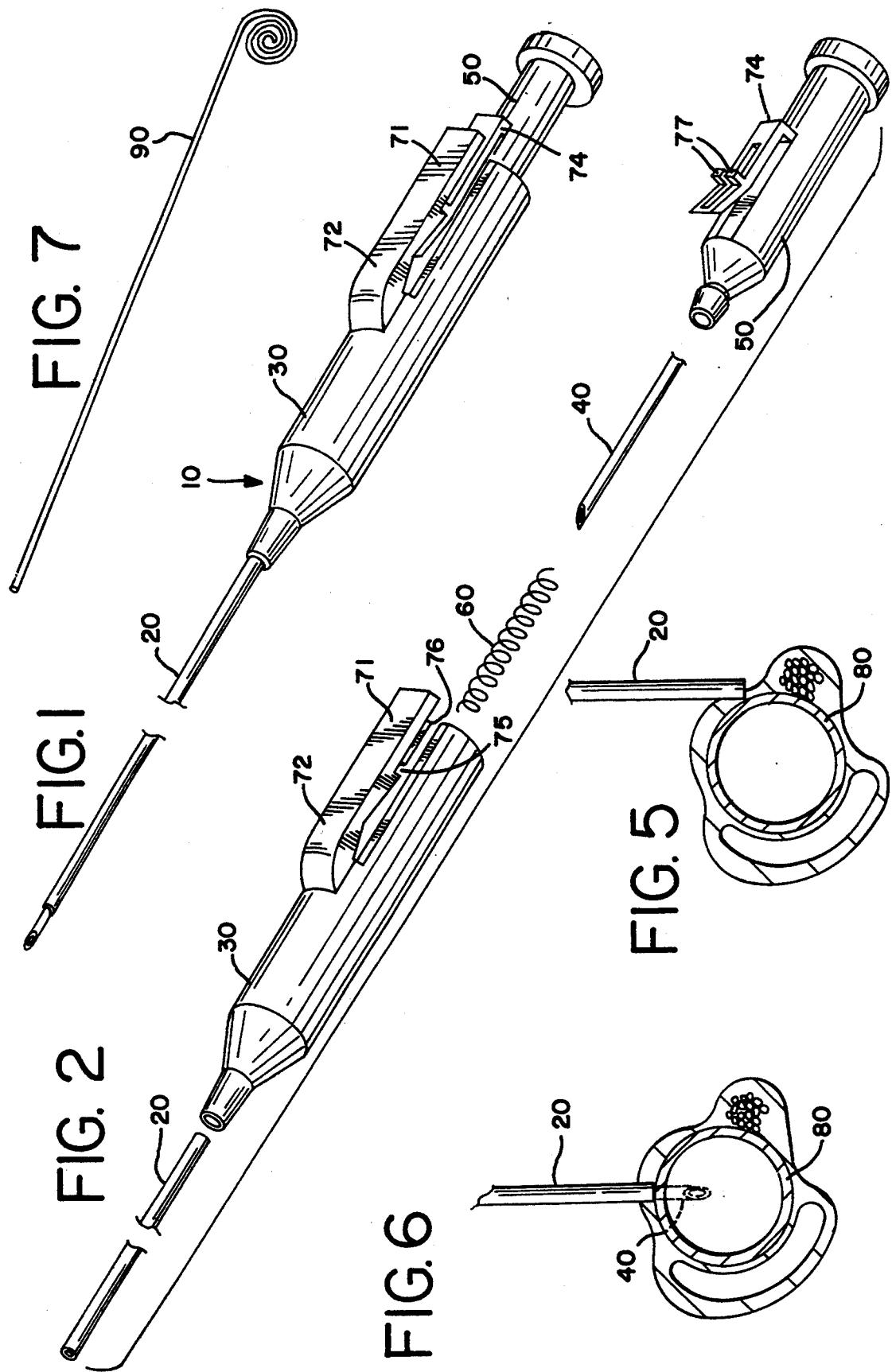

SELF-STICKING NEEDLE ASSEMBLY AND METHOD FOR INSERTION INTO AN ARTERY

BACKGROUND OF THE INVENTION

The present invention relates to needle assemblies, and more specifically, to needle assemblies used to enter the arterial system. The present invention also relates to methods of using a needle assembly to maximize the probability of puncturing the artery at its apex and avoiding back sticks.

The prior art is replete with various types of needle assemblies. Most prior art needles do not provide the user with any indication of where the needle tip is actually located. Often times the only signal evidencing arterial penetration is blood on the proximal end of the needle. This imprecise method commonly results in less than optimal needle placement, commonly referred to as "side sticks". A needle assembly providing information about arterial location would enable accurate needle placement thereby reducing the number of side sticks.

The absence of information relating to arterial location also presents problems once the needle has actually penetrated the artery. Because the user may be unaware of the exact moment of needle insertion, the needle is frequently advanced too far. Consequently, the needle may penetrate the back wall of the artery. This problem is commonly known as "back sticks." A needle assembly with a distance limiting feature that would restrict the travel of the needle would eliminate back sticks.

Side sticks and back sticks are particularly problems for procedures that involve catheterization of the artery, such as balloon angioplasty, especially where anticoagulants are present in the blood. The side stick problem is enhanced due to the introducer sheath or catheter being introduced from the wrong angle with respect to the artery. Back sticks allow bleeding out the back of the arterial wall. Of course, since the distance to the back wall of the artery is smaller the further one gets to the side of the artery, side sticks also increase the likelihood of back sticks.

Side sticks also present a problem for wound healing procedures when the catheterization or other procedure is completed. Direct pressure is not as effective when the puncture in the artery is on the side. Also, the various puncture sealing procedures being developed to aid in wound sealing, especially those disclosed in Application Ser. Nos. 08/055,634 and 07/873,955 (now abandoned), both of which are hereby incorporated by reference, are most effective when the vessel puncture is at or near the apex of the vessel.

One device currently on the market is the SmartNeedle TM vascular access device sold by the Peripheral Systems Group, An ACS ® company, 1395 Charleston Road, Mountain View, Calif. 94043. The device consists of a detachable probe situated inside the lumen of a standard 18 gauge introducer needle. During use, the probe is connected to a monitor that generates an audio output from a Doppler system located in the probe. The device is advertised as being useful for detecting and precisely locating blood flow within the anatomy. Evidently the audio output helps identify arterial and venous flow, the proximity of the probe to the vessel and when the needle and probe penetrate into the vessel. It is not certain whether the device can help eliminate side sticks and back sticks, but even if so, the device is expensive and requires cumbersome procedures for use.

For these reasons, an inexpensive and easy to use device and method that would decrease side stick and back stick incidents would be a significant improvement in the art.

SUMMARY OF THE INVENTION

The needle assembly of the present invention includes a rigid cannula with a blunt distal end, a needle housed inside the cannula, a hub on the needle for controlling the position of the distal end of the needle with respect to the distal end of the cannula and a stop connected to the cannula for limiting the distance of travel of the distal end of the needle. In the preferred embodiment, the needle assembly includes a spring attached to the needle hub.

The present invention also encompasses a method for inserting a needle assembly into a blood vessel, primarily an artery. In the first aspect, the method involves providing a needle assembly comprising a rigid cannula with a blunt distal end and a needle housed inside the cannula such that the distal end of the needle does not protrude past the distal end of the cannula. The needle assembly is then advanced into the body in the vicinity of an artery. The optimal puncture site of the artery is determined by maneuvering the needle assembly until a maximum pulsatile sensation is detected. Finally, the needle is moved within the cannula so that the needle projects past the distal end of the cannula and through the arterial wall.

In the second aspect, the method involves providing a needle assembly comprising a rigid cannula with a blunt distal end, a needle housed inside the cannula such that the distal end of the needle does not protrude past the distal end of the cannula and a stop connected to the cannula for limiting the distance of travel of the distal end of the needle. The needle assembly is then advanced into the body in the vicinity of the apex of a vessel. Finally, the needle is advanced within the cannula so that the needle projects past the distal end of the cannula and through the vessel wall. The stop is positioned such that the needle is prevented from sticking all the way through the vessel.

One of the advantages of the invention is that side sticks are reduced because information enabling optimal needle placement is provided. Another advantage lies in the elimination of back sticks due to the distance limiting feature. These and other advantages of the invention, as well as the invention itself, will be best understood in view of the attached drawings, a brief description of which follows:

BRIEF DESCRIPTION OF THE DRAWINGS

FIG. 1 is a perspective view of a preferred embodiment of the needle assembly of the present invention.

FIG. 2 is an exploded view of the needle assembly of FIG. 1.

FIG. 5 is a schematic representation of the needle of FIG. 1 at the side of an artery.

FIG. 6 is a schematic representation of the needle of FIG. 1 at the optimal puncture site of a femoral artery.

FIG. 7 is a plan view of a stylet optionally used with the needle assembly of FIG. 1.

DETAILED DESCRIPTION OF THE DRAWINGS AND PREFERRED EMBODIMENT OF THE INVENTION

Figure 3:
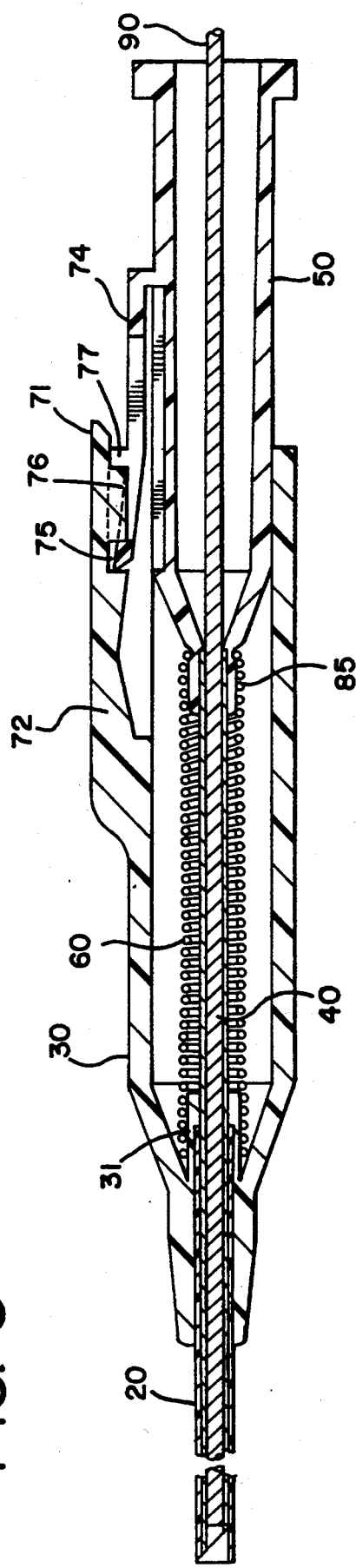
FIG. 3 is a cross-sectional view of the needle assembly of FIG. 1 in a first position.

Referring initially to FIG. 1, a preferred embodiment of the needle assembly of the present invention is disclosed. As illustrated, the needle assembly 10 includes a rigid cannula 20 having a blunt distal end. The cannula 20 is attached to a housing 30.

The needle assembly 10 also includes a needle 40. See FIG. 2. The needle 40 is attached to a hub 50 preferably located on the proximal end of the needle 40. In the preferred embodiment, the needle 40 has a standard noncoring tip. The needle 40 and attached hub 50 are inserted into the housing 30 and cannula 20. When the hub 50 is pulled back from the housing 30, the hub 50 and housing 30 interlock in a fashion that will be further described hereafter.

Turning to FIG. 3, in the preferred embodiment, a spring 60 is placed over the needle 40 and the distal end of the hub 50.

When the needle 40, hub 50 and spring 60 are placed into the housing 30 and cannula 20 and compressed together, the spring 60 rides up on spring seat 31 of the housing and spring seat 85 of hub 50. At that point the needle assembly 10 is completely assembled.

The embodiment of FIG. 1 also comprises a latching mechanism. The latching mechanism is comprised of two finger-like projections 72, 74 which extend respectively from the housing 30 and proximal hub 50. The finger-like projection 72 of the housing 30 extends from the middle of housing 30 toward its proximal end. The projection 74 of the hub 50 extends from the midportion of the hub 50 toward its distal end. The latching mechanism may assume any interlocking relationship. In the preferred embodiment, the distal underside of projection 72 angles slightly upward to just about the middle of the projection at which point the angle reverses and declines. A recess 75 is formed between the end of the decline and the proximal end of projection 72. A tab 76 is formed adjacent recess 75. Projection 72 also possesses a touch pad 71 which acts as the release for the latching mechanism.

Figure 4:
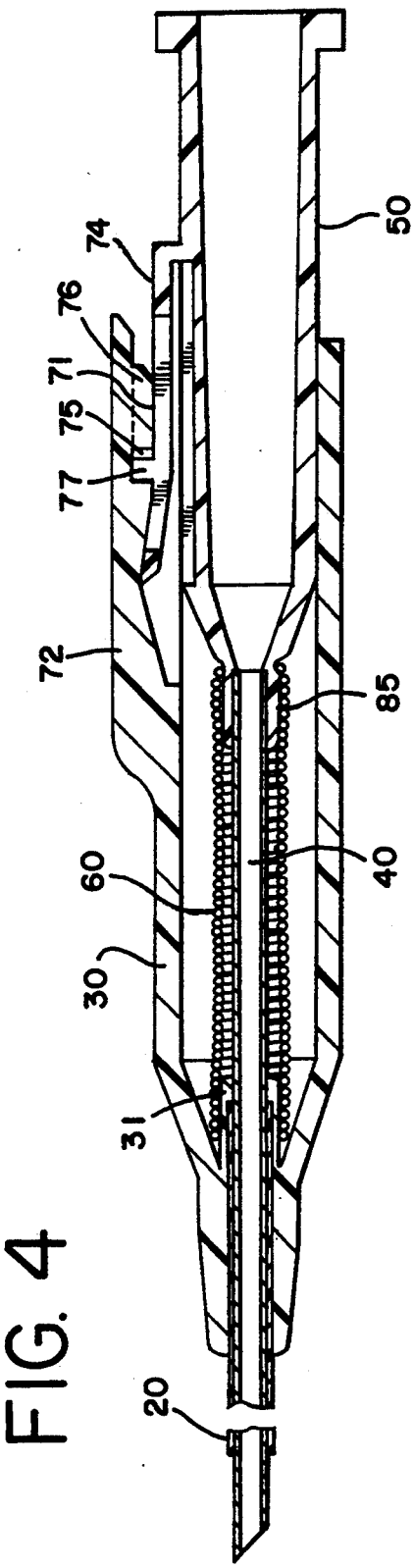
FIG. 4 is a cross-sectional view of the needle assembly of FIG. 1 in a second position.

Projection 74 is configured to assume an interlocking relationship with projection 72. In the preferred embodiment, the projection 74, extending from the hub 50, has a beveled distal end. When the hub 50 is pulled back from housing 30, the beveled tip automatically assumes a position in recess 75 of projection 72. See FIG. 3. When the latching mechanism is in the first position, the spring 60 is in an extended configuration and tabs 77 on projection 74 line up on either side of tab 76. Projection 74 has a middle bore extending over most of its length. Therefore, when the touch pad 71 of projection 72 is depressed, tabs 77 slide along tab 76 until tabs 77 meets the distal wall of recess 75 and are unable to proceed further. In this disengaged or second position, the spring 60 assumes a relaxed configuration and allows the distal end of said needle 40 to travel past the distal end of the cannula 20. See FIG. 4.

The invention also encompasses the method of using the above-described needle assembly 10. The needle assembly 10 is advanced into the body in the vicinity of an artery. The user then determines the optimal puncture site of the artery by maneuvering the needle assembly 10 until a maximum pulsatile sensation is detected. In the preferred embodiment, the pulsatile sensation is manually detected using the sense of touch. When the cannula 20 contacts the side of the artery 80, as shown in FIG. 5, the user will feel very little pulsatile sensation. However, when the cannula 20 rests on top of artery 80, the user will detect a stronger pulsatile sensation. When the maximum pulsatile sensation is detected, the user depresses touch pad 71. The release of the latching mechanism moves the needle 40 within the cannula 20 so that the distal end of the needle 40 projects past the distal end of the cannula 20 and through the arterial wall 80. A needle 40 entering an artery at the optimal puncture site is depicted in phantom lines in FIG. 6. After the needle has punctured the arterial wall 80, the user may insert an introducer wire. The introducer wire is then used as in standard catheterization procedures to guide an introducer and introducer sheath into the punctured artery, as is well known in the art.

One variation of the preferred embodiment includes the use of a stylet 90 (FIG. 7) which is inserted through the proximal end of needle 40 and extends through the entire assembly, as shown in FIG. 3, when the needle assembly 10 is ready for use. The stylet is preferably made of steel and is used to occupy the needle lumen until a maximum pulsatile sensation is detected. At that time, the stylet 90 would be removed and the needle 40 could be advanced through the arterial wall. The stylet is used to prevent tissue accumulation in the needle lumen.

Another variation of the preferred embodiment includes a cannula 20 attached to housing 30 and a needle 40 attached to a hub 50. This embodiment does not include a spring 60 or a latching mechanism. Instead, the assembly is manually operated when the user pushes the needle 40 and hub 50 toward the cannula 20 and housing 30. The internal cannula opening and hub 50 would then be sized to act as the distance limiting feature.

A third variation lies in arranging the cannula 20 and housing 30 in close approximation to the needle 40 and hub 50. In this arrangement, the needle 40 and cannula 20 may be side-by-side, as opposed to concentrically located.

The housing 30 may be manufactured from any type of rigid polymer. Preferably, the housing 30 is formed from medical grade, high impact polystyrene, more preferably from engineering grade polycarbonate such as GE Lexan #124R.

The cannula is preferably made of #304 stainless steel, with an outside diameter of 0.063 inches and an inside diameter of 0.056 inches. The cannula 20 is attached to housing 30 by any acceptable mechanical attachment is acceptable. Examples of feasible means of retention include, but are not limited to snap fitting, bondings welding, latching, screwing and pressing. In the preferred embodiment, the cannula 20 is insert molded into the housing 30.

Similarly, the needle 40 is preferably made of #304 stainless steel, insert molded into the hub 50. However, any means of mechanical retention of the needle 40 is also acceptable. The needle 40 may be of standard sizes and configurations, and preferably has a tip that is beveled in at least two directions, most preferably in three directions. The beveled section of the needle tip generally measures between 2 and 3 mm. In the preferred embodiment, the needle has an outside diameter of 0.052 inches and an inside diameter of 0.043 inches. It is also preferable that the needle lumen is large enough to accept a standard introducer wire. Standard introducer wires are generally in the range of 0.030–0.045 inches.

The spring 60 may comprise any type of medically approvable, biocompatible spring material. Preferably, the spring is stainless steel, more preferably, #304 stainless steel, and most preferably, an extension spring of #304 stainless steel with a 0.020 inch diameter wire and a spring force of up to 5 lbs. when the needle assembly is in its first position.

The instant invention provides many advantages over prior art needle assemblies. For example, the number of side sticks will be significantly reduced because the needle assembly provides the user with information relating to arterial location. See FIG. 6. The blunt distal end of the cannula 20 enables the user to probe the area without causing damage to the artery or adjacent tissue. The rigidness of the cannula 20 allows the pulsatile sensation to travel the length of the cannula 20 and ultimately reach the user. The user's ability to maneuver the needle assembly 10 until a maximum pulsatile sensation is detected ensures that the needle 40 will be placed in an optimal location in the artery.

A second advantage of the present invention lies in the distance limiting features this invention provides. This stop limits the distance the distal end of the needle 40 can travel in the forward direction. When used in the common femoral artery, the parts are preferably sized so that the distal tip of needle 40 extends 8 mm beyond the distal end of cannula 20 when the housing 30 and hub 50 are in their second position. Likewise, due to the beveled tip of the needle 40, the beginning of the needle opening will be 5–6 mm beyond the distal tip of the cannula 20 when the housing 30 and hub 50 are in their second position. This eliminates the occurrence of back sticks, yet allows the needle to travel far enough to penetrate the vessel wall, even if there is plaque deposited on the arterial wall. The stop may be provided by either the relaxed position of spring 60 or by the second position of the latching mechanism. Preferably the parts are sized and assembled such that the solid height of the spring 60 in the assembled mode places the needle 40 in the same position as when the tab 77 of the projection 74 is engaged in the recess 75 of projection 72. Then both the spring and the latching mechanism together limit the distance that the distal end of the needle 40 may travel. The latching mechanism in the first position not only holds the distal tip of needle 40 inside cannula 20, it also limits the distance the needle 40 is allowed to travel in the backward direction, to prevent the device from unintentionally being pulled apart when being set in its first position.

It will be appreciated that the foregoing has set forth various illustrative and preferred embodiments of the principles of the present invention, but that numerous alternatives and modifications such as the use of a compression spring mounted between modified parts, will occur to those of ordinary skill in the art without departure from the spirit or the scope of the present invention.

We claim:

1. A needle assembly comprising:
   a) a rigid cannula with a blunt distal end;
   b) a needle having a sharp distal end housed inside said cannula;
   c) a hub on said needle for controlling the position of the distal end of said needle with respect to the distal end of said cannula; and
   d) a stop connected to said cannula, wherein when the distal end of said needle is forced past the distal end of said cannula and into a vessel, said stop limits the distance the distal end of said needle may travel past the distal end of said cannula.

2. The needle assembly of claim 1 further comprising a first position latching mechanism for holding said needle in a first position with respect to said cannula wherein the distal tip of the needle is inside the cannula.

3. The needle assembly of claim 2 wherein said first position latching mechanism comprises projections extending from the housing and the hub in an opposing manner such that said projections interlock in said first position.

4. The needle assembly of claim 2 wherein said first position latching mechanism further comprises a release mechanism which disengages said first position latching mechanism and allows the distal end of said needle to travel past the distal end of the cannula.

5. The needle assembly of claim 2 further comprising a spring attached to said hub for forcing the distal end of said needle through the distal end of said cannula.

6. The needle assembly of claim 5 wherein said spring is in an extended configuration when said first position latching mechanism is engaged.

7. The needle assembly of claim 5 wherein said spring is in a relaxed configuration when said first position latching mechanism is disengaged.

8. The needle assembly of claim 1 further comprising a two-position latching mechanism which situates said needle with respect to said cannula in a first position, wherein the distal end of said needle does not protrude past the distal end of said cannula, and second position, wherein the distal end of said needle protrudes past the distal end of said cannula.

9. The needle assembly of claim 8 wherein said two position latching mechanism comprises projections which extend from the housing and the hub in an opposing fashion such that said projections interlock.

10. The needle assembly of claim 8 wherein said two position latching mechanism further comprises a release mechanism which disengages said latching mechanism from said first position and allows the distal end of said needle to travel until said latching mechanism becomes engaged in said second position.

11. The needle assembly of claim 10 further comprising a spring attached to said hub.

12. The needle assembly of claim 11 wherein said spring is in an extended configuration when said two position latching mechanism is engaged in said first position.

13. The needle assembly of claim 11 wherein said spring is in a relaxed configuration when said two position latching mechanism is engaged in said second position.

14. The needle assembly of claim 1 wherein said needle is hollow.

15. The needle assembly of claim 1 wherein said needle has a beveled tip.

16. The needle assembly of claim 1 further comprising a spring attached to said hub.

17. The needle assembly of claim 1 further comprising a stylet placed through the lumen of the needle.

18. The needle assembly recited in claim 1 wherein said stop limits the distance the distal end of said needle may travel past the distal end of said cannula to about 8 mm.

19. A needle assembly comprising:

a) a housing with a finger-like projection extending from its mid portion toward its proximal end;
b) a rigid cannula with a blunt distal end attached to said housing;
c) an inner hub within said housing with a finger-like projection extending from its mid portion toward its distal end;
d) a needle molded onto said inner hub, said inner hub assembly placed so that the finger-like projections on the housing and hub engage each other; and
e) a spring encompassing said needle such that the proximal end of said spring rests on the distal end of said inner hub assembly.

20. A method for inserting a needle through an arterial wall to minimize side sticks and optimize the probability of the needle being inserted at the apex of the artery comprising the steps of:
   a) providing a needle assembly comprising:
      i) a rigid cannula with a blunt distal end; and
      ii) a needle housed inside said cannula such that the distal end of said needle does not protrude past the distal end of said cannula when in a retracted position;
   b) advancing said needle assembly into the body in the vicinity of an artery while in said retracted position;
   c) determining the optimal puncture site of the vessel by maneuvering said needle assembly until a maximum pulsatile sensation is detected; and
   d) moving said needle within said cannula from said retracted position so that said needle projects past the distal end of said cannula and through the arterial wall.

21. A method for inserting a needle as recited in claim 19 further comprising the steps of:
   a) inserting a styler into the needle lumen before said step of advancing said needle assembly, and
   b) removing the styler from the needle lumen after said step of determining the optimal puncture site.

22. A method for inserting a needle as recited in claim 19 wherein maneuvering said needle assembly comprises contacting the artery with said cannula and moving it to various positions in order to determine said maximum pulsatile sensation.

23. A method for inserting a needle as recited in claim 19 wherein the pulsatile sensation is caused by expansion and contraction of the artery.

24. A method for inserting a needle as recited in claim 19 wherein said maximum pulsatile sensation is detected using the sense of touch.

25. A method for inserting a needle through a vessel wall to eliminate back sticks comprising the steps of:
   a) providing a needle assembly comprising:
      i) a rigid cannula with a blunt distal end,
      ii) a needle housed inside said cannula such that the distal end of said needle does not protrude past the distal end of said cannula when the needle assembly is in a retracted position, and
      iii) a stop connected to said cannula for limiting the distance of travel of the distal end of said needle;
   b) advancing said needle assembly into the body in the vicinity of the apex of a vessel while in said retracted position; and
   c) moving said needle within said cannula from said retracted position so that said needle projects past the distal end of said cannula and through the vessel wall, the stop being positioned such that the needle is prevented from sticking all the way through the vessel.

26. A method for inserting a needle as recited in claim 25 further comprising the steps of:
   a) inserting a stylet into the needle lumen before said step of advancing said needle assembly; and
   b) removing the stylet before said step of moving said needle within said cannula.

* * * * *

UNITED STATES PATENT AND TRADEMARK OFFICE
CERTIFICATE OF CORRECTION

PATENT NO. : 5,425,718
DATED : June 20, 1995
INVENTOR(S) : Sew-Wah Tay et al.

It is certified that error appears in the above-indentified patent and that said Letters Patent is hereby corrected as shown below:

<u>On the Title Page</u>

In column 2, line 23 under "References Cited U.S. PATENT DOCUMENTS" delete "5,221,628" and substitute --5,211,628--.

<u>In the Detailed Description of the Drawings and Preferred Embodiment of the Invention</u>

In column 4, line 54 delete "bondings" and substitute --bonding,--.

Col. 7, In claim 21, line 36, delete "styler" and substitute --stylet--.

Col. 8, In claim 21, line 1, delete "styler" and substitute --stylet--.

Signed and Sealed this

Twenty-seventh Day of August, 1996

Attest:

BRUCE LEHMAN

*Attesting Officer*   *Commissioner of Patents and Trademarks*